United States Patent
Blacker et al.

[11] Patent Number: 6,142,339
[45] Date of Patent: *Nov. 7, 2000

[54] AEROSOL DISPENSING DEVICE

[75] Inventors: Richard Blacker; Daniel K. Engelbreth; James N. Schmidt, all of London, Canada

[73] Assignee: 1263152 Ontario Inc., London, Canada

[*] Notice: This patent issued on a continued prosecution application filed under 37 CFR 1.53(d), and is subject to the twenty year patent term provisions of 35 U.S.C. 154(a)(2).

[21] Appl. No.: 09/008,184

[22] Filed: Jan. 16, 1998

[51] Int. Cl.⁷ ........................................................ B67D 5/06
[52] U.S. Cl. ................................ 222/23; 222/36; 222/38; 128/200.23
[58] Field of Search ......................... 128/200.23; 222/36, 222/38, 23

[56] References Cited

U.S. PATENT DOCUMENTS

| | | |
|---|---|---|
| Re. 34,847 | 2/1995 | Muderlak et al. . |
| 165,054 | 6/1875 | Baldwin . |
| 498,851 | 6/1893 | Jones . |
| 1,219,858 | 3/1917 | Patterson . |
| 2,455,962 | 12/1948 | Wheeler et al. . |
| 2,580,292 | 12/1951 | Geary et al. . |
| 2,587,147 | 2/1952 | Guion et al. . |
| 2,630,027 | 3/1953 | Wunderlich . |
| 2,644,452 | 7/1953 | Brown . |
| 2,767,680 | 10/1956 | Lermer . |
| 2,883,086 | 4/1959 | Davison et al. . |
| 2,939,597 | 6/1960 | Greene . |
| 2,943,730 | 7/1960 | Tregilgas . |
| 2,953,242 | 9/1960 | Shaw . |
| 3,073,468 | 1/1963 | Arneson . |
| 3,085,745 | 4/1963 | Auberger . |

(List continued on next page.)

FOREIGN PATENT DOCUMENTS

| | | |
|---|---|---|
| 598250 B2 | 6/1990 | Australia . |
| 535518 | 1/1957 | Canada . |
| 0 028 929 A2 | 5/1981 | European Pat. Off. . |
| 0 098 939 A2 | 1/1984 | European Pat. Off. . |
| 0 114 617 A2 | 8/1984 | European Pat. Off. . |
| 0 063 599 B1 | 6/1986 | European Pat. Off. . |
| 0 230 323 B1 | 7/1987 | European Pat. Off. . |
| 0 236 871 A2 | 9/1987 | European Pat. Off. . |
| 0 269 496 A2 | 6/1988 | European Pat. Off. . |
| 0 488 609 A1 | 6/1992 | European Pat. Off. . |
| 0 559 757 B1 | 9/1993 | European Pat. Off. . |
| 6 603 758 | 7/1969 | Germany . |
| 27 02 539 A1 | 1/1977 | Germany . |
| 3336486 A1 | 4/1984 | Germany . |
| 8 590 143 | 10/1985 | Germany . |
| 998148 | 7/1965 | United Kingdom . |
| 1058636 | 2/1967 | United Kingdom . |

*Primary Examiner*—Kevin Shaver
*Assistant Examiner*—David Deal
*Attorney, Agent, or Firm*—Brinks Hofer Gilson & Lione

[57] ABSTRACT

An aerosol dispenser for dispensing metered dosages of medicaments from a container having a valve stem extending longitudinally therefrom and moveable between an open and closed position. The container is reciprocally moveable within the housing along a longitudinal axis. The housing has a well adapted to receive the valve stem and an exhaust port. The well communicates with the port such that the metered dosage of medicament is dispensed through the port when the valve stem is moved to the open position. A worm is rotatably mounted in the housing about an axis transverse to the longitudinal axis and is responsive to the movement of the reciprocal movement of the container within the housing such that the longitudinal movement causes the worm to rotate about its axis. An indicator member includes dosage indicia visible to a user and a circular gear mounted in the housing about an axis transverse to the axis of the worm and to the longitudinal axis. The circular gear engages the worm. In a preferred embodiment, the indicator assembly is provided in an indicator module. A method for dispensing measured dosages includes the steps of moving the container along the longitudinal axis so as to cause the worm to rotate about its axis, which causes the worm gear to rotate about its axis.

54 Claims, 6 Drawing Sheets

U.S. PATENT DOCUMENTS

| | | |
|---|---|---|
| 3,119,557 | 1/1964 | Chapman . |
| 3,120,318 | 2/1964 | Rigor . |
| 3,148,801 | 9/1964 | Radeloff et al. . |
| 3,151,599 | 10/1964 | Livingston . |
| 3,170,597 | 2/1965 | Reichenberger . |
| 3,187,963 | 6/1965 | Anderson . |
| 3,191,867 | 6/1965 | Helms . |
| 3,334,731 | 8/1967 | Dale . |
| 3,344,951 | 10/1967 | Gervais . |
| 3,419,187 | 12/1968 | Bazarnic . |
| 3,446,179 | 5/1969 | Bender . |
| 3,477,561 | 11/1969 | Espinal . |
| 3,495,567 | 2/1970 | Hayes et al. . |
| 3,511,409 | 5/1970 | Huck . |
| 3,549,057 | 12/1970 | Perez . |
| 3,572,282 | 3/1971 | Tump et al. . |
| 3,589,563 | 6/1971 | Carragan et al. . |
| 3,612,349 | 10/1971 | Thomas . |
| 3,655,952 | 4/1972 | Johnson et al. . |
| 3,688,945 | 9/1972 | Harman, Jr. et al. . |
| 3,753,417 | 8/1973 | Garby . |
| 3,766,882 | 10/1973 | Babbitt, III . |
| 3,796,348 | 3/1974 | Zipper . |
| 3,797,748 | 3/1974 | Nozawa et al. . |
| 3,802,608 | 4/1974 | Gullett . |
| 3,831,808 | 8/1974 | Bender . |
| 3,831,812 | 8/1974 | Dolan . |
| 3,845,883 | 11/1974 | Johnson et al. . |
| 3,848,774 | 11/1974 | Schimke . |
| 3,886,879 | 6/1975 | Frost et al. . |
| 3,887,099 | 6/1975 | Gillman et al. . |
| 3,921,568 | 11/1975 | Fish . |
| 3,926,326 | 12/1975 | Grau . |
| 3,960,713 | 6/1976 | Carey . |
| 3,977,554 | 8/1976 | Costa . |
| 3,994,421 | 11/1976 | Hansen . |
| 4,011,829 | 3/1977 | Wachsmann et al. . |
| 4,029,033 | 6/1977 | Kerwin et al. . |
| 4,034,757 | 7/1977 | Glover . |
| 4,037,719 | 7/1977 | Perlmutter . |
| 4,069,935 | 1/1978 | Hampel . |
| 4,069,942 | 1/1978 | Marshall et al. . |
| 4,078,661 | 3/1978 | Thomas . |
| 4,094,408 | 6/1978 | Ford . |
| 4,162,746 | 7/1979 | Anderson et al. . |
| 4,164,301 | 8/1979 | Thayer . |
| 4,188,984 | 2/1980 | Lyall . |
| 4,220,247 | 9/1980 | Kramer . |
| 4,291,688 | 9/1981 | Kistler . |
| 4,300,548 | 11/1981 | Jones . |
| 4,345,541 | 8/1982 | Villa-Real . |
| 4,347,804 | 9/1982 | Villa-Real . |
| 4,347,853 | 9/1982 | Gereg et al. . |
| 4,350,265 | 9/1982 | Griffiths et al. . |
| 4,354,621 | 10/1982 | Knickerbocker . |
| 4,357,192 | 11/1982 | Moser . |
| 4,365,722 | 12/1982 | Kramer . |
| 4,405,045 | 9/1983 | Villa-Real . |
| 4,419,016 | 12/1983 | Zoltan . |
| 4,432,300 | 2/1984 | Lyss . |
| 4,436,223 | 3/1984 | Wilson . |
| 4,440,306 | 4/1984 | Van Buskirk et al. . |
| 4,489,834 | 12/1984 | Thackrey . |
| 4,500,005 | 2/1985 | Forrester . |
| 4,501,370 | 2/1985 | Kelley . |
| 4,511,150 | 4/1985 | Seguenot . |
| 4,523,933 | 6/1985 | Laush et al. . |
| 4,528,933 | 7/1985 | Allen . |
| 4,534,345 | 8/1985 | Wetterlin . |
| 4,538,744 | 9/1985 | Weissenborn . |
| 4,548,157 | 10/1985 | Hevoyan . |
| 4,562,933 | 1/1986 | Dennis . |
| 4,565,302 | 1/1986 | Pfeiffer et al. . |
| 4,634,012 | 1/1987 | Kelley . |
| 4,637,528 | 1/1987 | Wachinski et al. . |
| 4,641,759 | 2/1987 | Kelley . |
| 4,646,936 | 3/1987 | Frazier et al. . |
| 4,662,520 | 5/1987 | Griffin . |
| 4,664,107 | 5/1987 | Wass . |
| 4,666,051 | 5/1987 | Trick . |
| 4,668,218 | 5/1987 | Virtanen . |
| 4,677,975 | 7/1987 | Edgar et al. . |
| 4,693,399 | 9/1987 | Hickman et al. . |
| 4,705,182 | 11/1987 | Newel-Lewis . |
| 4,722,729 | 2/1988 | Dettbarn et al. . |
| 4,723,673 | 2/1988 | Tartaglia et al. . |
| 4,727,886 | 3/1988 | Conrardy et al. . |
| 4,736,871 | 4/1988 | Luciani et al. . |
| 4,749,093 | 6/1988 | Trick . |
| 4,753,189 | 6/1988 | Mastman et al. . |
| 4,756,423 | 7/1988 | Holtsch . |
| 4,782,966 | 11/1988 | Thackrey . |
| 4,792,664 | 12/1988 | Schwab . |
| 4,817,822 | 4/1989 | Rand et al. . |
| 4,890,572 | 1/1990 | Huang . |
| 4,934,358 | 6/1990 | Nilsson et al. . |
| 4,947,875 | 8/1990 | Brooks et al. . |
| 4,955,371 | 9/1990 | Zamba et al. . |
| 4,969,578 | 11/1990 | Gander et al. . |
| 4,984,158 | 1/1991 | Hillsman . |
| 5,009,338 | 4/1991 | Barker . |
| 5,011,032 | 4/1991 | Rollman . |
| 5,020,527 | 6/1991 | Dessertine . |
| 5,038,972 | 8/1991 | Muderlak et al. . |
| 5,069,204 | 12/1991 | Smith et al. . |
| 5,082,129 | 1/1992 | Kramer . |
| 5,082,130 | 1/1992 | Weinstein . |
| 5,115,929 | 5/1992 | Buono . |
| 5,174,473 | 12/1992 | Marelli . |
| 5,184,761 | 2/1993 | Lee . |
| 5,188,251 | 2/1993 | Kusz . |
| 5,190,643 | 3/1993 | Duncan et al. . |
| 5,209,375 | 5/1993 | Fuchs . |
| 5,224,474 | 7/1993 | Bloomfield . |
| 5,227,764 | 7/1993 | Umemoto . |
| 5,228,586 | 7/1993 | Fuchs . |
| 5,242,067 | 9/1993 | Garby et al. . |
| 5,243,970 | 9/1993 | Ambrosio et al. . |
| 5,261,548 | 11/1993 | Barker et al. . |
| 5,263,475 | 11/1993 | Altermatt et al. . |
| 5,284,133 | 2/1994 | Burns et al. . |
| 5,289,946 | 3/1994 | Fuchs . |
| 5,299,701 | 4/1994 | Barker et al. . |
| 5,300,042 | 4/1994 | Kossoff et al. . |
| 5,301,873 | 4/1994 | Burke et al. . |
| 5,328,597 | 7/1994 | Boldt, Jr. et al. . |
| 5,331,953 | 7/1994 | Andersson et al. . |
| 5,335,823 | 8/1994 | Fuchs et al. . |
| 5,349,945 | 9/1994 | Wass et al. ........................ 128/200.23 |
| 5,356,012 | 10/1994 | Tang et al. . |
| 5,363,842 | 11/1994 | Mishelevich et al. . |
| 5,370,267 | 12/1994 | Schroeder . |
| 5,382,243 | 1/1995 | Mulholland . |
| 5,388,572 | 2/1995 | Mulhauser et al. . |
| 5,392,768 | 2/1995 | Johansson et al. . |
| 5,394,866 | 3/1995 | Ritson et al. . |
| 5,397,028 | 3/1995 | Jesadanont . |
| 5,411,173 | 5/1995 | Weinstein . |
| 5,421,482 | 6/1995 | Garby et al. . |
| 5,437,270 | 8/1995 | Braithwaite . |
| 5,448,042 | 9/1995 | Robinson et al. . |
| 5,482,030 | 1/1996 | Klein . |

| | | | | | | |
|---|---|---|---|---|---|---|
| 5,505,192 | 4/1996 | Samiotes et al. | | FOREIGN PATENT DOCUMENTS | | |
| 5,505,195 | 4/1996 | Wolf et al. | | | | |
| 5,509,905 | 4/1996 | Michel. | 1 290 484 | 9/1972 | United Kingdom. | |
| 5,519,197 | 5/1996 | Robinson et al. | 1317315 | 5/1973 | United Kingdom. | |
| 5,520,166 | 5/1996 | Ritson et al. | 2 063 075 | 6/1981 | United Kingdom. | |
| 5,544,647 | 8/1996 | Jewett et al. | 2 092 991 | 8/1982 | United Kingdom. | |
| 5,549,101 | 8/1996 | Trofast et al. | 2 104 393 | 3/1983 | United Kingdom. | |
| 5,564,414 | 10/1996 | Walker et al. | 2 191 032 | 12/1987 | United Kingdom. | |
| 5,611,444 | 3/1997 | Garby et al. | 2 195 544 | 4/1988 | United Kingdom. | |
| 5,617,844 | 4/1997 | King. | WO 86/02275 | 4/1986 | WIPO. | |
| 5,622,163 | 4/1997 | Jewett et al. | WO 87/04354 | 7/1987 | WIPO. | |
| 5,625,334 | 4/1997 | Compton. | WO 90/10470 | 9/1990 | WIPO. | |
| 5,625,659 | 4/1997 | Sears. | WO 91/06334 | 5/1991 | WIPO. | |
| 5,638,970 | 6/1997 | Garby et al. | WO 92/07600 | 5/1992 | WIPO. | |
| 5,657,748 | 8/1997 | Braithwaite. | WO 92/09324 | 6/1992 | WIPO. | |
| 5,676,129 | 10/1997 | Rocci, Jr. et al. | WO 92/15353 | 9/1992 | WIPO. | |
| 5,687,710 | 11/1997 | Ambrosio et al. | WO 92/17231 | 10/1992 | WIPO. | |
| 5,694,882 | 12/1997 | Marshall. | WO 93/24167 | 12/1993 | WIPO. | |
| 5,718,355 | 2/1998 | Garby et al. | WO 94/11272 | 5/1994 | WIPO. | |
| 5,724,957 | 3/1998 | Rubsamen et al. | WO 95/34874 | 12/1995 | WIPO. | |
| 5,732,836 | 3/1998 | Barker et al. | WO 96/16687 | 6/1996 | WIPO. | |
| 5,799,651 | 9/1998 | Garby et al. | | | | |
| 6,029,659 | 2/2000 | O'Connor. | | | | |

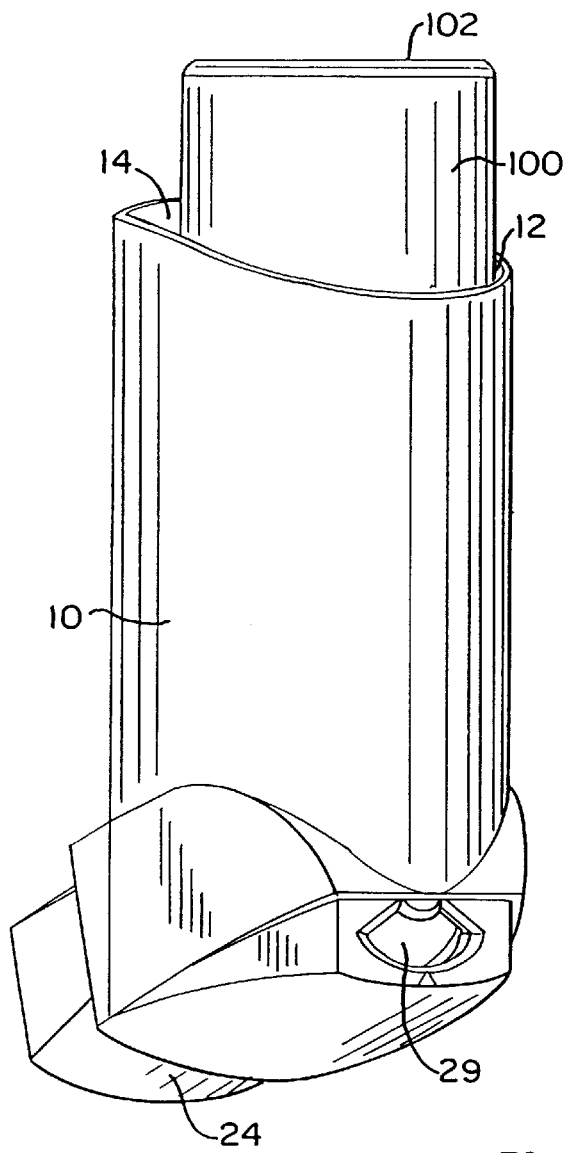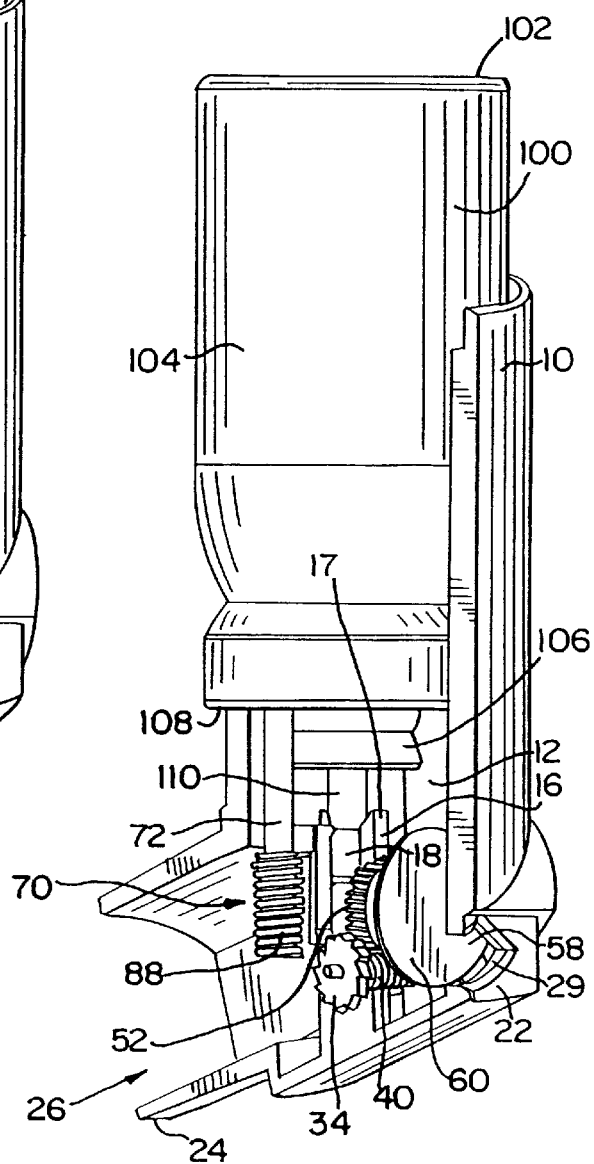

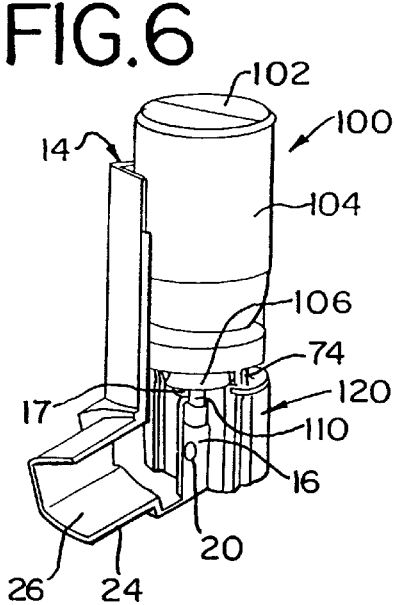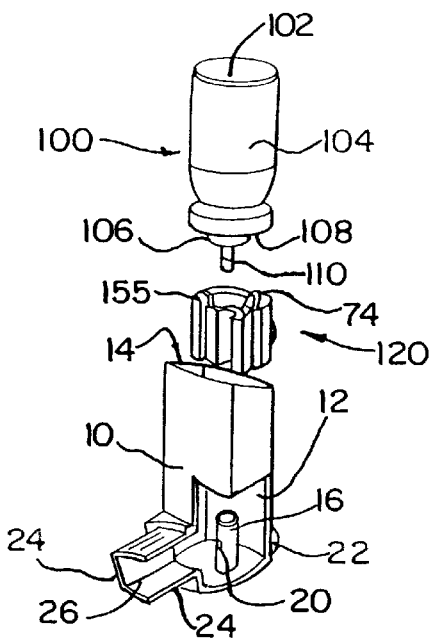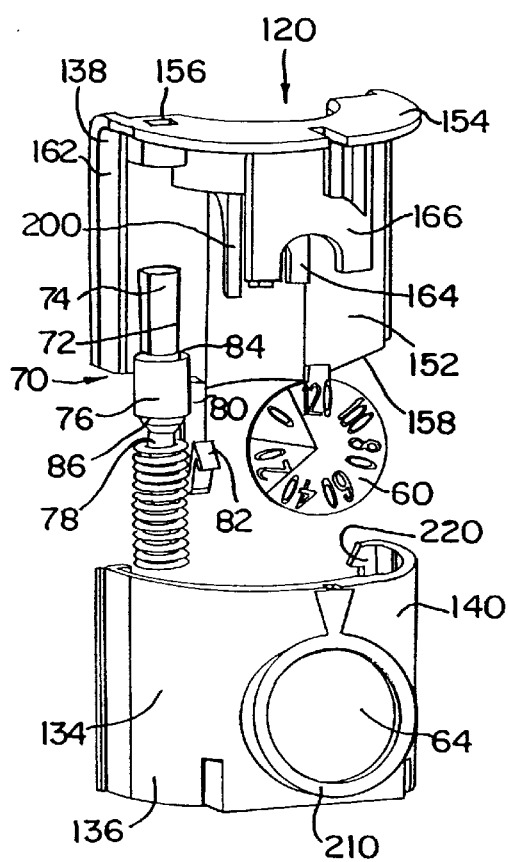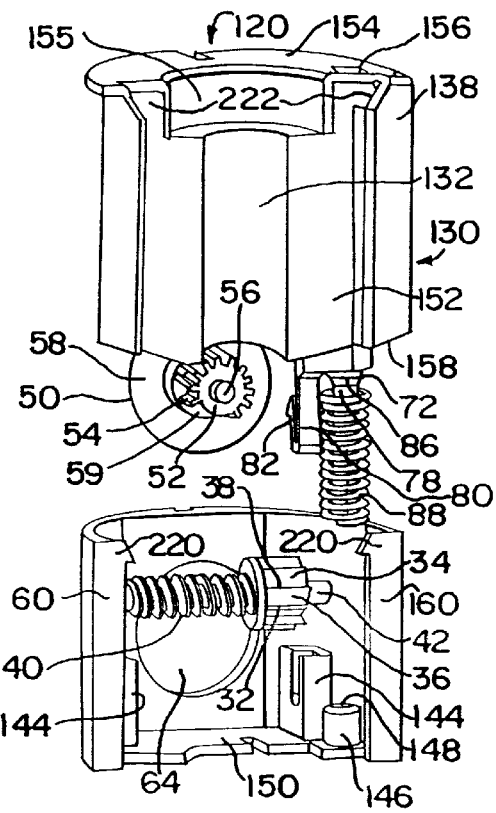

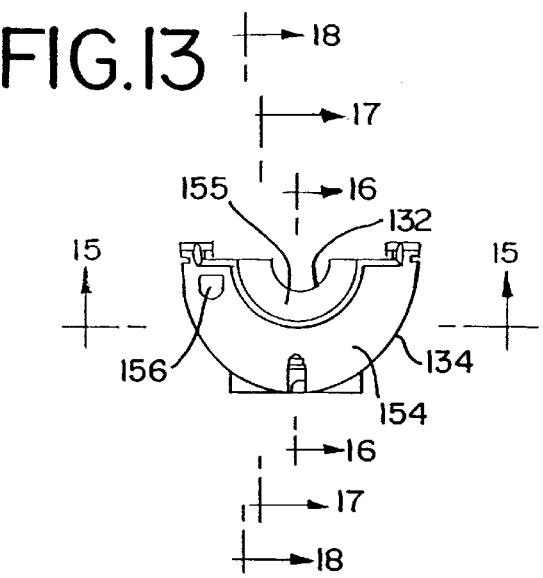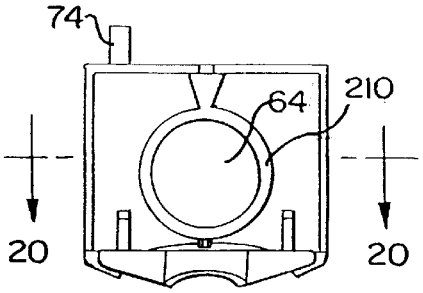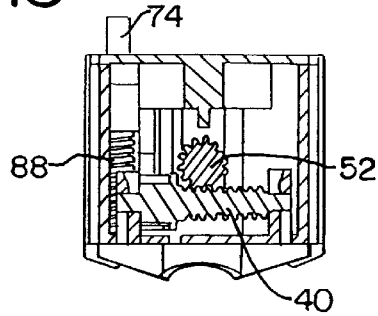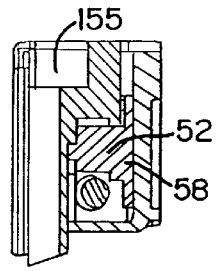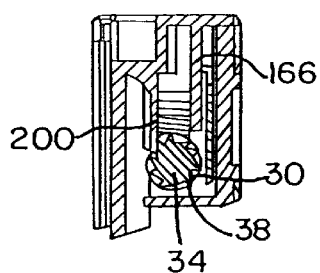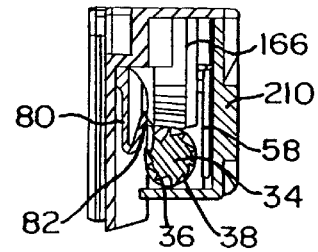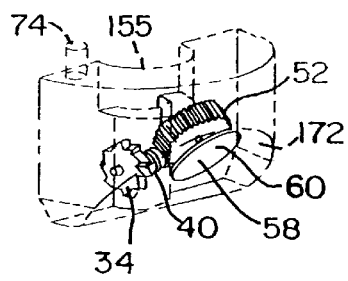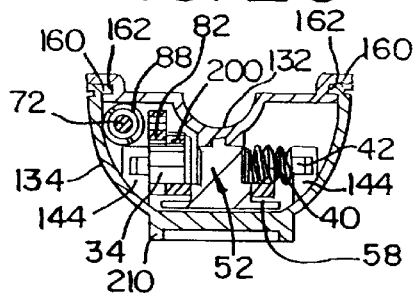

AEROSOL DISPENSING DEVICE

BACKGROUND OF THE INVENTION

The present invention relates generally to an aerosol dispensing device, and in particular, to an aerosol dispensing device having an improved dosage indicator for indicating the number of metered dosages that have been dispensed from, or remain in, the dispensing device.

Aerosol dispensing devices have been developed that include a counting or dose indicating device to indicate the number of metered doses that have been dispensed from the device, or to indicate the number of doses remaining therein. For example, patients have certain conditions that can be treated with medicaments dispersed in an aerosol and administered to the patient by inhalation. In one format, the aerosol and medicaments are contained in a canister, or container, and dispensed in metered, or measured, dosages with an inhalation device, or actuator boot. In such an arrangement, it is important for the patient to be able to ascertain the number of metered doses remaining in the canister, either by an indication of the number remaining therein or by knowledge of the number already dispensed therefrom, such that the patient is not caught unaware with an empty canister when in need of the medicament. Thus, it may be important for the inhalation device to provide an accurate indication of either the number of doses remaining in the canister, or the number of doses already dispensed therefrom.

Typically, a conventional aerosol canister includes a body and a valve stem which can be depressed relative to the body so as to emit the metered dose of aerosol and medicament. The canister is usually supplied with a predetermined number of metered doses, generally on the order of about 200, such that the counting of the number of valve stem depressions, and corresponding number of dispensed metered doses, can be directly correlated with the number of doses remaining in the canister.

In operation, the canister is typically received within a housing of the inhalation device, wherein the valve is brought into engagement with a support block in the housing. The user administers the medicament by moving the canister relative to the housing so as to depress the valve stem and internal valve and thereby release a metered dose, which is typically administered to the user through a port or mouthpiece extending from the housing. After the dose is administered, the valve stem, which is typically spring loaded, biases the canister away from the support block so as to again move the canister relative to the housing. In this way, a metered dose of medicament is administered by each cycle of linear reciprocal movement of the canister relative to the housing.

Some actuator boots have indicating devices that convert the linear reciprocal movement of the canister relative to the housing into a one-way, or single-cycle, movement of an indicator, wherein the indicator identifies the relative fullness of the canister, the number of metered doses remaining therein or the number of doses already administered. Although these actuator boots with indicators have provided the advantage of generally being able to keep track of the number of dosages, there remains room for improvement. For example, indicating devices of this nature may include complex moving parts which can be difficult to assemble and expensive to manufacture. Such devices may also be susceptible to counting inaccuracies due to the configuration of the indexing or mating parts, or require excessive amounts of space within the housing to accommodate the relatively large or numerous moving parts. Others still may impede or interfere with the airflow and medicament being dispensed from the inhalation device. Alternatively, some devices use electrical circuitry to count or record the dispersements. Such devices can be relatively expensive to manufacture, however, and require electrical power and may be more susceptible to damage in various environments, such as moist conditions.

SUMMARY OF THE INVENTION

Briefly stated, the invention is directed to an aerosol dispenser for dispensing metered dosages of medicaments from a container having a valve stem extending longitudinally therefrom, wherein the valve stem is moveable between a closed position and an open position. The container dispenses a metered dosage when the valve stem is moved to the open position. The dispenser includes a housing adapted to support the container reciprocally moveable within the housing along a longitudinal axis. The housing has a well adapted to receive the valve stem and an exhaust port. The well communicates with the port such that the metered dosage of medicament is dispensed through the port when the valve stem is moved to the open position. A worm is rotatably mounted in the housing about an axis transverse to the longitudinal axis and is responsive to the movement of the reciprocal movement of the container within the housing such that the longitudinal movement of the container relative to the housing causes the worm to rotate about its axis. An indicator member includes dosage indicia visible to a user and a circular gear mounted in the housing about an axis transverse to the axis of the worm and non-parallel to the longitudinal axis. The circular gear engages the worm.

In a preferred embodiment of the invention, a ratchet wheel is rotatably mounted in the housing and is adapted to be responsive to the reciprocal movement of the container relative to the housing along the longitudinal axis. The ratchet wheel is connected to the worm such that rotation of the ratchet causes the worm gear to rotate about its axis. In addition, an actuator member including an arm is preferably mounted within the housing and is adapted to move in response to the movement of the container and operably engage the ratchet wheel so as to rotate the wheel in response to the longitudinal movement of the container relative to the housing. Also in the preferred embodiment, the indicator member includes an indicator wheel coaxially mounted with the circular gear on an axle defining the axis of rotation of the indicator member. The dosage indicia are applied to a surface of the indicator wheel.

In another aspect of the invention, the ratchet wheel, worm, actuator member and indicator member are mounted within an indicator module which is adapted to be mounted within the dispenser housing. The module preferably including a first and second member which are joined to form an enclosure or housing, and which support the ratchet wheel, worm, actuator member and indicator member therein.

In another aspect of the invention, a key member is mounted to the container and is shaped to be received in a recess formed in the module housing.

In yet another aspect of the invention, a method is provided for dispensing measured dosages from the container. The method includes the steps of moving the container along the longitudinal axis so as to move the valve stem to the open position wherein a metered dosage is discharged. The longitudinal movement of the container within the housing causes the ratchet gear to rotate a predetermined angular amount, which, in turn, causes the worm to rotate about its axis. The worm then engages the circular worm gear of the indicator member so as to rotate the worm gear about its axis.

In yet another aspect, a method is provided for assembling a dispenser comprising a housing, a container and a dose counter module.

The present invention provides significant advantages over other aerosol dispensing devices. In particular, the worm provides for a compact drive component that does not occupy excess space within the housing. Moreover, the worm provides for high gear reduction ratios while maintaining a continuous engagement with the circular worm gear. The continuous engagement of the worm and circular gear ensures that the accuracy of the counting device is maintained, while simultaneously simplifying the manufacturing and assembly process.

The use of a circular gear having an axis non-parallel, and preferably transverse or perpendicular to the longitudinal movement of the container within the housing, also provides several advantages. Importantly, the gear can be easily mounted to the housing with an inexpensive and easy-to-install axle. Thus, the circular gear provides for a compact single-cycle device that fits easily into the housing, and which maintains continuous engagement with the worm gear for improved and accurate indexing of the indicator member. Moreover, the components are arranged so as to not interfere with or otherwise impede the air flow from the valve stem to the exhaust port of the housing. In addition, the indicator wheel, which is preferably coaxially mounted with the worm gear, provides an ideal planar surface for displaying the dosage indicia. The indicia can be easily viewed by the user through the viewing window.

The module also presents several advantages. In particular, the self-contained unit can be separately manufactured and installed as needed in any number of conventional types of dispensing devices with minimal modification of the housing. Moreover, the module can be easily installed without interfering with or otherwise impeding the air flow from the valve stem to the exhaust port and ultimately to the patient.

The key member also presents several advantages. In particular, differently configured key members can be installed on containers holding different medicaments so as to prevent the user from interchanging various medicament containers in the dispenser and thereby alter the number of doses being counted.

The present invention, together with further objects and advantages, will be best understood by reference to the following detailed description taken in conjunction with the accompanying drawings.

BRIEF DESCRIPTION OF THE DRAWINGS

FIG. 4 is a perspective view of an alternative embodiment of the dispensing device.

FIG. 5 is a perspective view of the dispensing device shown in FIG. 4 with a portion of the housing cut away.

FIG. 6 is a perspective view of a container, a dispenser housing and an indicator module with a portion of the housing cut away.

FIG. 7 is an exploded perspective view of a container, a dispenser housing and an indicator module with a portion of the housing cut away.

FIG. 8 is an exploded perspective view of the indicator module.

FIG. 9 is an exploded perspective view of the indicator module from the opposite side as shown in FIG. 8.

FIG. 13 is a top view of the indicator module.

FIG. 14 is a rear view of the indicator module.

FIG. 15 is a cross-sectional view taken along line 15—15 of FIG. 13.

FIG. 16 is a cross-sectional view taken along line 16—16 of FIG. 13.

FIG. 17 is a cross-sectional view taken along line 17—17 of FIG. 13.

FIG. 18 is a cross-sectional view taken along line 18—18 of FIG. 13.

FIG. 19 is a perspective view of an alternative embodiment of the module.

FIG. 20 is a cross-sectional view taken along line 20—20 of FIG. 14.

DETAILED DESCRIPTION OF THE PRESENTLY PREFERRED EMBODIMENTS

Figure 1:
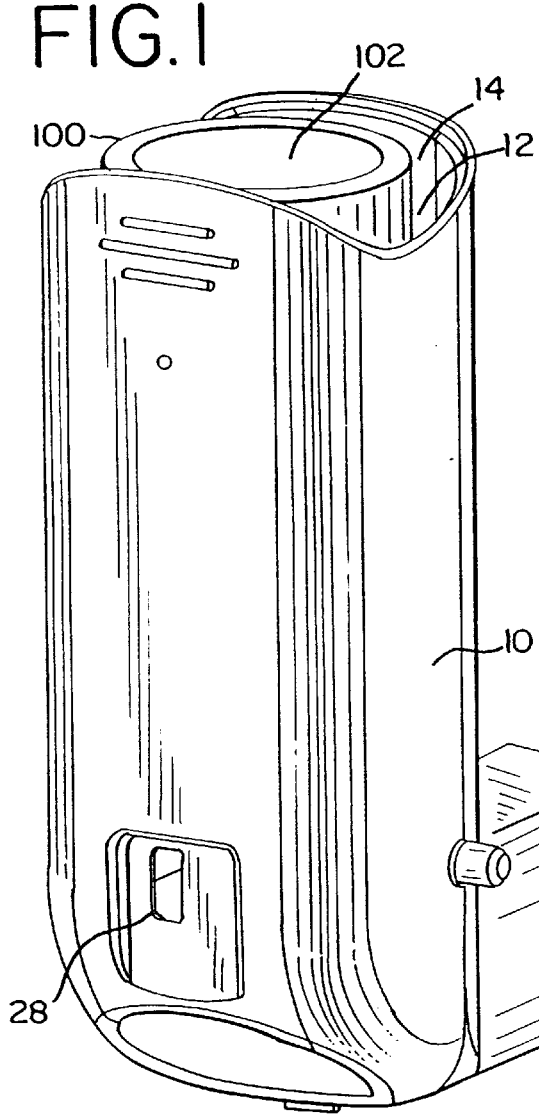
FIG. 1 is a perspective view of a dispensing device with a viewing window revealing dosage indicia.

Referring to the drawings, and in particular FIGS. 1, 4, 6 and 7, an aerosol dispenser is shown as including a housing 10, or actuator boot, and a container 100 disposed therein. The housing has a longitudinally extending cavity 12 shaped to receive the container. A top portion of the housing is generally open such that the container can be inserted in the housing through opening 14 and be installed therein with a bottom end 102 of the container protruding from the housing and exposed to the user for actuation.

The term "longitudinal" as used herein is intended to indicate the direction of the reciprocal movement of the container relative to the housing. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa.

As shown in FIGS. 5, 6 and 7, a cylindrical support block 16 having a well 18 is formed in a bottom portion 22 of the housing. An orifice 20 penetrates the support block to communicate with a bottom portion of the well. A mouthpiece 24, intended for insertion into the mouth of a patient, forms an exhaust port 26 that communicates with the orifice and well. The mouthpiece 24 extends laterally from the housing so as to facilitate insertion of the mouthpiece into the mouth of the patient.

The container 100 is formed as a cylindrical canister 104 having a 106 hub disposed on a top surface 108 thereof. A valve stem 110 extends longitudinally from the hub. The valve stem extends coaxially from the canister and is biased outwardly therefrom by a spring (not shown) mounted within the canister. The container 100 is mounted in the housing by press fitting the valve stem 110 in the well 18 of the support block.

In a preferred embodiment, the container 100 is filled with a pressurized aerosol and medicament which is dispensed therefrom in specific metered doses by depressing or moving the valve stem 110 from an extended closed position to a depressed open position. A single metered dose is dispensed from the container by each reciprocal, longitudinal movement of the valve stem.

In operation, the opening of the valve stem is effected by moving the container 100 reciprocally within the housing 10 along a longitudinal axis, defined by the valve stem and the reciprocal movement of the container, by depressing the exposed bottom end 102 of the canister relative to the housing so as to move the valve stem 110 to the open position as it is supported within the well by the support block. As the valve stem is moved to the open position, the container dispenses a metered dose of aerosol and medicament through the well 18 and orifice 20 and into the exhaust port. The aerosol and medicament are then transmitted to the patient through the exhaust port of the mouthpiece by way of either a self-generated or assisted airflow.

In a preferred embodiment, the container 100 is intended to dispense a predetermined number of metered doses of medicament. For example, conventional inhaler containers typically hold on the order of 100 to 200 metered doses. In operation, it is important that the patient be aware of the number of metered doses remaining in the container such that the patient is not caught unaware with an empty canister when in need of the medicament.

Figure 2:
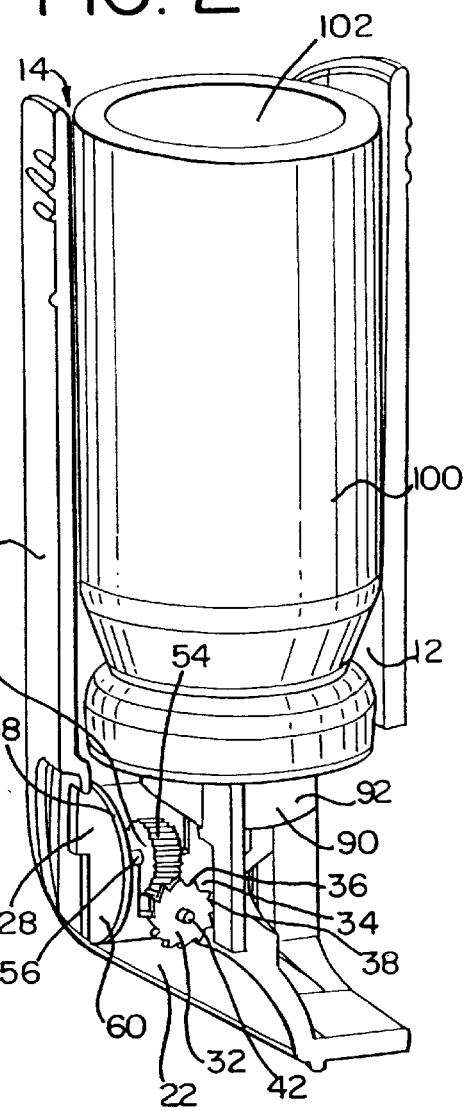
FIG. 2 is a perspective view of the dispensing device with a portion of the housing cut away.
Figure 3:
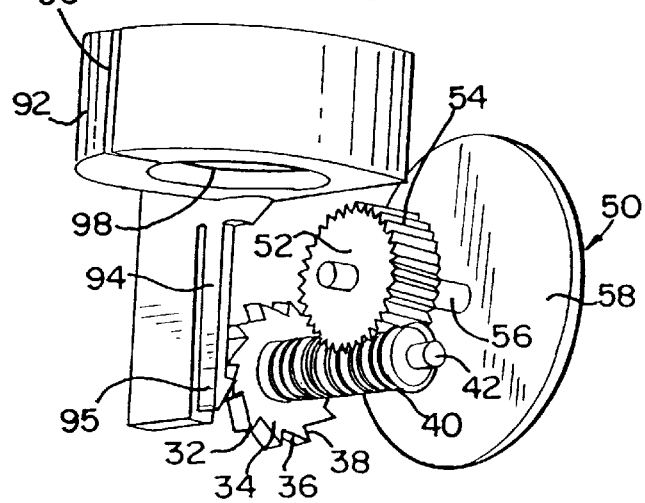
FIG. 3 is a perspective view of the indicator assembly.

Now referring to FIGS. 2 and 3, an aerosol dispenser is shown as including a housing, a container mounted therein as described above and an indicator assembly. The indicator assembly includes a ratchet gear 32 coaxially mounted with a worm 40 on an axle 42 in a lower portion of the housing. A plurality of teeth 34 are formed about the periphery of the ratchet gear. The teeth 34 are cut or formed with a tapered surface 36 and engagement surface 38. In a preferred embodiment, the ratchet and worm are formed out of a hard durable plastic. It should be understood, however, that other materials such as metal would also work. The ratchet and worm can be made as separate parts, or molded as a single integral member.

In a preferred embodiment, the axle 42 and worm 40 define an axis of rotation transverse, or perpendicular, to the longitudinal axis defined by the valve stem and reciprocal movement of the container relative to the housing. Opposite ends of the axle 42 are rotatably supported in the housing.

Also as shown in FIGS. 2 and 3, an indicator member 50 comprises a circular worm gear 52 and indicator wheel 58 coaxially mounted on an axle. In a preferred embodiment, the axle 56 defines an axis of rotation transverse to the axis defined by the worm and also transverse to the longitudinal axis defined by the reciprocal movement of the container relative to the housing. The axle 56 is rotatably supported in the housing. Teeth 54 are formed around the periphery of the worm gear 52 and are shaped to permanently engage the worm 40. As shown in FIG. 2, the indicator wheel 58 has a planar face 60 which is exposed to the patient through a viewing window 28 formed in the housing.

Figure 12:
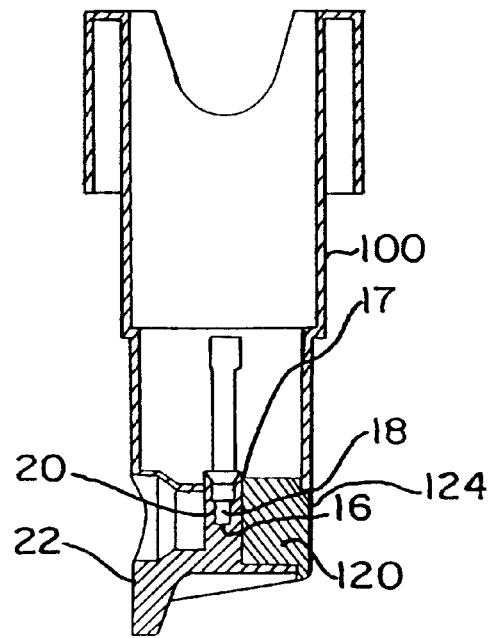
FIG. 12 is a section cut of a housing and an indicator module mounted therein.

The ratchet gear 32, worm 40, worm gear 52 and indicator wheel 58 provide an ideal arrangement for indicating the number of doses remaining in the container, or the number dispensed therefrom. In particular, relatively high reduction ratios are made possible through use of the ratchet, worm and worm gear without the corresponding requirement of providing extremely fine teeth on one or more of the ratchet gear and worm gear. Moreover, the worm and worm gear interface avoids the associated inaccuracies introduced by the mating, and potential skipping, of conventional spur gears having fine teeth. Furthermore, the installation of the indicator member is effected by the installation of a simple axle which can be supported in a plurality of positions and angular orientations within the housing. Importantly, the high reduction ratio realized with the worm 40 allows for the worm gear 52 to have a relatively small diameter, such that it can be easily mounted within small spaces within the housing. Indeed, as shown in FIGS. 6 and 12, the entire indicator assembly can be mounted behind the support block 16 and below the upper surface 17 thereof such that the assembly does not interfere with the dispensing of the medicament from the orifice or with the airflow generated by the patient in administering the medicament.

Referring to FIG. 5, an actuator member 70 is configured as a post member 72 moveably supported in the housing along an axis parallel to the longitudinal axis defined by the reciprocal movement of the container within the housing. In an alternative embodiment shown in FIGS. 7–9, the post member includes an upper portion 74, a middle portion 76 and a lower portion 78. A resilient arm member 80 extends from the middle portion of the post member and terminates in a tapered hook member 82 shaped to selectively engage one of the ratchet wheel teeth. The middle portion 76 is defined by upper and lower stop surface 84, 86. A spring 88 is disposed about the lower portion 78 of the post member and engages the lower stop surface 86 so as to bias the actuator member upwardly against the top surface 108 of the canister as shown in FIG. 7. Although a compression spring is shown in the Figures, it should be understood that cantilever, torsion, leaf and tension springs would also work to bias the actuator member upwardly into engagement with the container. The springs can be made of metal or plastic.

In an alternative embodiment, shown in FIGS. 2 and 3, actuator member 90 includes locking ring 92 and a resilient arm member 94 extending longitudinally downwardly therefrom. A longitudinal slit 96 is formed in the locking ring so as to allow for the locking ring 92 to be expanded and disposed around the hub 106 (shown in FIG. 5) of the canister in a snap fit configuration such that the valve stem of the container extends through opening 98 of the locking ring. A distal end of the resilient arm member terminates in a hook member 95 which is shaped to selectively engage the teeth of the ratchet wheel.

In the operation of the preferred embodiment shown in FIGS. 6–9, 13–18 and 20, the container is moved longitudinally within the housing so as to depress the valve stem to the open position as explained above. As the container is moved downwardly within the housing, the actuator member 70 is moved longitudinally downward such that the hook member 82 engages the ratchet wheel and rotates it a predetermined angular amount corresponding to the pitch of the teeth. When the container is released by the patient, the spring (not shown) within the canister biases the container upwardly within the housing along the longitudinal axis such that the valve stem 110 is moved to the closed position within the container. As the container moves upwardly, the resilient arm member 80 is biased laterally outward as a tapered end portion of the hook member 82 slides against the tapered surface 36 of one of the ratchet teeth. As the container and resilient arm member reach the top of the stroke, wherein the valve stem is moved completely to the closed position, the resilient arm member 80 returns to its normal straightened configuration as the hook member 82 slips past the tapered surface of one of the teeth so as to be positioned over the engagement surface 38 of that tooth 34 for the next cycle.

Alternatively, the operation of the ratchet wheel can be reversed as shown in FIG. 3. In this embodiment, the resilient arm member 94 is biased outwardly by the tapered surface of one of the ratchet gear teeth on the downstroke. At the bottom of the stroke, the hook member 95 slips into an underlying relationship with the engagement surface of the tooth. When the container is released by the patient, the spring (not shown) within the canister biases the container upwardly within the housing along the longitudinal axis such that the valve stem is moved to the closed position within the container. As the container moves upwardly with respect to the housing, the resilient arm member 94 moves longitudinally upward such that the hook member 95 engages the engagement surface 38 of one of the teeth and thereby rotates the ratchet wheel an incremental amount.

In the preferred embodiment shown in FIGS. 6–9, 13–18 and 20, it is the force of the spring 88 that moves the arm member 80 upwardly so as to return the actuator member in preparation for another cycle. In the alternative embodiment shown in FIGS. 2 and 3, it is the movement of the canister, as it is biased upwardly by the internal spring acting on the valve stem, that causes the locking ring 92 and arm member 94 to move upwardly and thereby rotate the ratchet gear.

Referring to FIGS. 8 and 17, a resilient non-return member engages the ratchet gear adjacent the hook member so as to ensure that the rotation of the ratchet gear is unidirectional. Alternatively, the non-return member can be positioned to engage the ratchet gear opposite the actuator arm member. The non-return member includes an end portion adapted to engage the engagement surface of the ratchet gear teeth. As the ratchet gear is rotated by the actuator, the non-return member slides along the tapered surface of one of the teeth of the ratchet wheel and does not interfere with the rotation thereof.

The rotation of the ratchet gear causes the worm 40 to rotate a desired predetermined amount. It should be understood that the desired amount of rotation is dependent upon the diameter of the ratchet wheel and the number of teeth positioned thereabout. Rotation of the worm, which permanently engages the teeth of the worm gear, causes the worm gear and indicator wheel to rotate a predetermined incremental amount. The amount of rotation of the indicator wheel is dependent upon the pitch of the worm, the number of worm threads and the pitch of the worm gear and the number of worm gear teeth. In a preferred embodiment, the worm has a single thread.

For ease of manufacturing, it is desirable to provide as coarse a pitch on each of the ratchet and worm gears as possible, although the gears are still defined as fine-toothed gears. However, it is also intended that the indicator member make only a single revolution (single-cycle) corresponding to a complete evacuation of medicament from the container. Thus, when a large number of doses (on the order of 200) are contained within the canister, it is important for the ratchet, worm and worm gear to provide a relatively high reduction ratio, such that 200 linear reciprocal movements of the actuator member correspond to one or less revolutions of the indicator member. Because the ratchet gear and worm rotate together, it should be understood that the number of teeth on the ratchet gear and worm gear, and the number of threads of the worm, determine the ultimate reduction ratio between the rotation of the ratchet gear and the rotation of the indicator wheel.

For example, when the container holds 240 metered doses, an acceptable ratio is realized if the ratchet is made relatively coarse with 10 teeth and the worm gear is provided with 28 teeth. In operation, the dispensing of 10 metered doses will cause the worm to make one complete revolution so as to thereby move the worm gear one tooth. After 240 linear reciprocal movements, the worm gear has been advanced by 24 teeth. Extra teeth are provided so that the starting and ending indicia, indicating a relative fullness or emptiness of the container respectively, are not labeled one on top of the other.

In a preferred embodiment, shown in FIGS. 9 and 15, the worm gear has teeth formed around only a portion of its periphery so that a gap is formed between the teeth around the remaining portion of the periphery. In operation, the gears are configured so that the worm disengages from the last tooth of the worm gear as the final prescribed dose of medicament is dispensed. In this position, the indicia on the indicator wheel will indicate to the user that the canister is empty. Therefore, although the user can continue to move the canister so as to open the valve, the resultant movement of the actuator, ratchet gear and worm will not in turn rotate the indicator member as the gap in the teeth on the worm gear results in the disengagement of the worm and worm gear. In this way, the indicator wheel is prevented from being inadvertently rotated from a full to empty reading and then back again to a full reading, which could confuse the user about the number of doses remaining in the canister.

Figure 10:
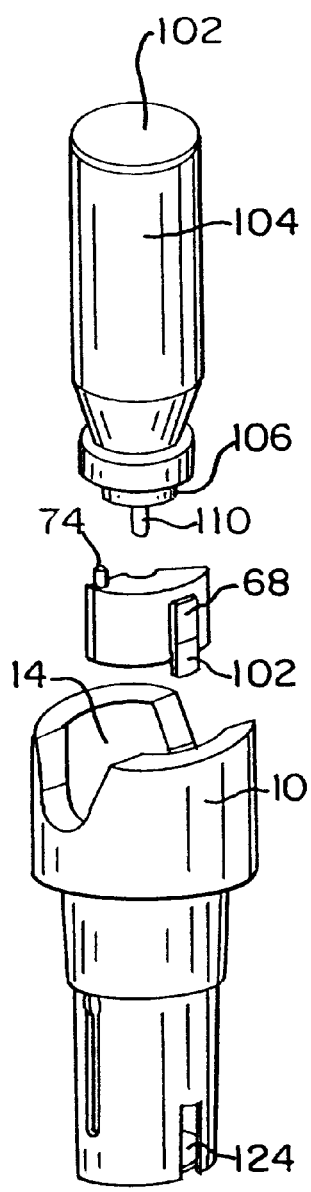
FIG. 10 is an exploded perspective view of a container, and an alternative embodiment of the dispenser housing and the indicator module.

The indicator wheel 58, indicia 66 and viewing window 28 can be arranged in a variety of configurations for viewing by the user. For example, the viewing window 28, 124 can be configured as a rectangular shaped window as shown in FIG. 2 or 10 respectively, as an arcuate shaped window 29 as shown in FIG. 4, wherein approximately ⅓ of the face of the indicator wheel is visible at any time, as a circular shaped window (not shown) or as any other shape allowing the user to view the indicator wheel and the indicia located thereon. In one embodiment, the indicia take the form of a color code, where, for example, a portion of the wheel is colored green to indicate the starting full position, a portion is colored yellow to indicate a medium fullness and a portion is colored red to indicate that the container is empty. Obviously, other colors, shading or alpha-numerical indicia can be provided on the indicator wheel to indicate the relative fullness or emptiness of the container.

In an alternative embodiment, the indicator wheel can be oriented within the housing such that either its planar face or its circumferential surface, with indicia applied thereto, are visible to the user through the exhaust port of the mouthpiece.

In a preferred embodiment of the dispenser, shown in FIGS. 6–10, 13–18 and 20, the indicator assembly is arranged in an indicator module 120. The indicator module 120 is shaped to be received within the housing where it is disposed around a portion of the support block 16. In particular, the support block is spaced apart from the wall of the dispenser housing, otherwise referred to as the actuator boot, so as to form a donut-shaped socket in the bottom of the housing. The module includes a module housing 130 having an inner concave surface 132 that is shaped to mate with an outer convex surface of the cylindrical support block and an outer convex 134 surface that is shaped to mate with the inner concave surface of the housing which is also generally cylindrical. In this way, the module housing is shaped to be received within the socket formed around the support block. Preferably, the module housing has a semicircular shape and fits around a portion of the support block opposite the orifice opening so as to not interfere with the dispensing of the medicament, or the airflow transmitting the medicament to the patient. In this way, the module is maintained rearwardly of the midpoint of the support block.

As shown in FIGS. 8–9, the module preferably includes a face portion 210 that extends from the rear convex surface of the module and includes a module viewing window 64. The face portion snaps into the housing viewing window opening (circular opening not shown) so as to secure the module thereto. As shown in an alternative embodiment in FIGS. 10–12, the face portion includes a rectangular viewing window 68 and a downwardly extending locking member 122 which extends through the dispenser viewing window opening 124 and engages a bottom wall of the housing. It should be understood, however, that the module can be secured within the housing by any number of conventional means, including the use of fasteners or adhesive. Alternatively, the module can simply be press fit into the socket formed between the support block and housing wall.

In the embodiment shown in FIG. 8, the circular viewing window 64 is provided in the module housing so as to expose a substantial portion of the planar indicator wheel. Numerical indicia, corresponding to the number of doses in the container, are provided on the face 60 of the indicator wheel. An arrow, or like indicator, is applied to the housing adjacent the viewing window and provides an indication of the number of doses remaining in the housing, or the number dispensed therefrom, as the indicator wheel is rotated.

Figure 11:
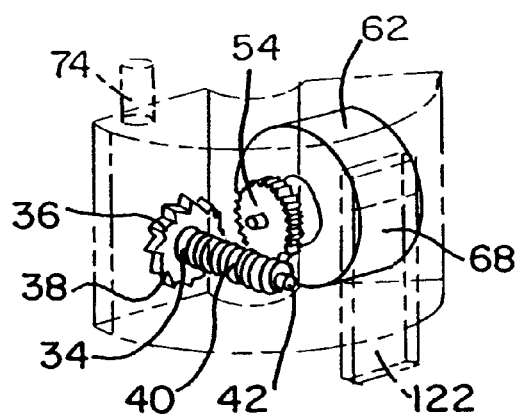
FIG. 11 is a perspective view of the alternative embodiment of the indicator module shown in FIG. 10.

In another alternative embodiment, shown in FIGS. 10 and 11, the indicia are applied to a circumferential surface 62 of the indicator wheel. The module viewing window 68, which is preferably rectangular, and indicator wheel are arranged such that the circumference, or periphery, of the wheel is visible through the module and dispenser viewing windows. As with the other embodiments, the indicia can take the form of color coding, shading, alpha-numerical characters and the like.

As shown in FIGS. 6–10, 13–18 and 20, the indicator assembly, or worm, worm gear, ratchet gear and indicator member, are mounted within the module housing 130. The housing is preferably formed from a first and second cover member 136, 138, although it should be understood that a single, integral piece of material would also work, as would any plurality of members joined together. The first cover member 136 has a vertical wall 140 defining the outer convex surface 134 shaped to mate with the inner surface of the housing as described above. The secondary viewing window 142 of the module is provided in the vertical wall 140 so as to be aligned with the viewing window of the housing when the module is installed therein. The viewing window is framed by the face portion. The first member also includes a pair of opposing bearing seats 144 formed on an inner surface of the vertical wall. The bearing seats 144 are shaped to support the ends of axle 42. A post member 146 extends upwardly from a base 150 of the first member adjacent one of the bearing seats and has a socket 148 formed coaxially therein.

The second cover member 138 mates with the first cover 136 to form an enclosure therebetween. The second cover member includes a vertical wall 152, a portion of which defines the concave surface 132 shaped to mate with the outer surface of the support block. An upper horizontal flange 154 extends from the vertical wall 152 and mates with the vertical wall of the second member in overlying relationship therewith so as to close off the top of the module. The upper flange 154 has an opening 156 formed therein which is shaped to receive the upper portion 74 of the post member. In one embodiment, the upper surface of the flange is maintained parallel with or below the top surface of the support block so as not to interfere with the container as it is depressed toward the support block. Alternatively, the module housing is provided with a semi-circular recess 155 shaped to receive the hub as the container is actuated whereby the surface 108 of the container engages the upper portion 74 and the surface 108 is positioned adjacent to the surface 154 of the module housing when the valve is moved to the open position. A bottom edge 158 of the vertical wall mates with the base 130 of the first cover member to close off the bottom of the module. The cover members are joined by slidably engaging vertical flanges 160 on the first cover member with grooves 162 formed on the second cover member. Inwardly extending tabs 220 snap fit into slots 222 formed in the second cover member. Alternatively, it should be understood that the first and second cover members can be joined with fasteners, adhesive and the like.

When the cover members are assembled to form the module housing, the upper portion 74 of the post member extends through the opening in the upper flange of the first cover member and engages the top surface 108 of the container, which is inverted in the housing. Alternatively, the actuator member can be attached to the hub of the container with the locking ring as previously described. In such an embodiment, the arm member of the actuator member extends downwardly from the ring through the opening in the top of the first cover member and is positioned to selectively engage the ratchet gear. The insertion of the arm in the opening prevents the canister and attached locking ring from being rotated so as to move the arm member out of position for selective engagement with the ratchet gear.

The lower portion 78 of the post member is moveably received within the socket 148 formed in the post member 146 extending from the base of the second cover member. Spring 88 is disposed about the lower portion 78 and includes a lower end mounted on the post member 146. The upper end of the spring engages the lower stop surface 86 of the post member 72. The spring biases the post member upwardly within the housing such that the upper portion 74 protrudes through the opening and into engagement with the top surface of the container 108.

The worm 40 and ratchet gear 32 are rotatably supported on the bearing seats 144 formed in the second member. Preferably, opposite ends of axle 42 are snap fitted into the bearing seats. The indicator member 50 is rotatably supported by the second cover member such that the worm gear engages the worm when the cover members are joined together. In particular, the second cover includes a pair of downwardly opening lug members 164, 166. The axle 56 of the indicator member is received in the first lug member 164 and a hub portion 59 positioned between the worm gear and the indicator wheel is received within the second lug member 166. Preferably, the axle and hub are snap fitted into the lugs, but are permitted to freely rotate therein. When the cover members are joined, the indicator member, and in particular the worm gear, are trapped between the lug members and the worm.

It should be understood that in the alternative embodiment of FIGS. 2–5, the supporting structure for the worm and ratchet, including the bearing seats or like supports, and the supporting structure for the indicator member, including the lug members, are similar to the structure provided in the module housing, but are integrally molded into the housing. Similarly, a post and socket member can be intergrally molded into the bottom of the housing so as to support the actuator member and spring.

In an alternative embodiment shown in FIG. 19, a lower portion 172 the outer vertical wall of the module housing is angled so as to a mate with a housing having a similar angled planar bottom surface. As shown in FIG. 19, the axis of rotation of the indicator member is oriented at an angle of approximately 45 degrees from the longitudinal axis so that the face of the indicator wheel 60 is substantially parallel to the angled surface of the housing. A viewing window is provided in the angled surface 172 and is aligned with a similar viewing window provided in the angled wall of the dispenser housing.

Figure 21:
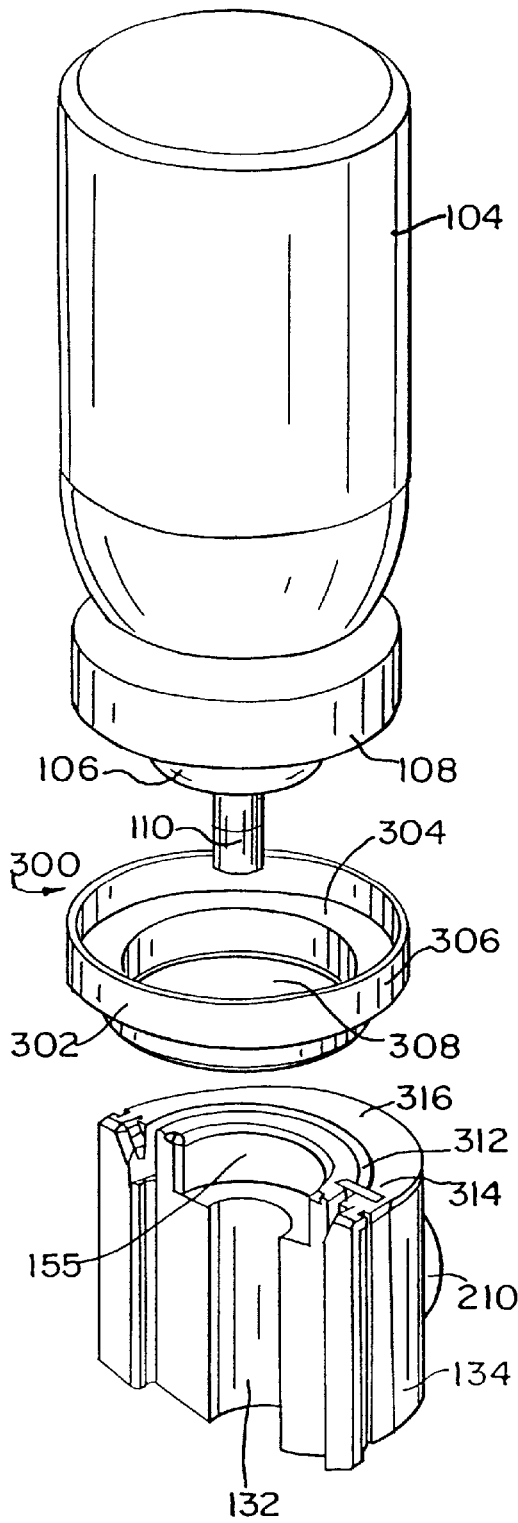
FIG. 21 is an exploded view of a container, a key member and an indicator module.
Figure 23:
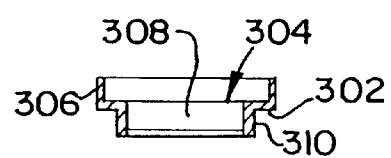
FIG. 23 is a cross-sectional view of the key member taken along line 23—23 of FIG. 22.
Figure 22:
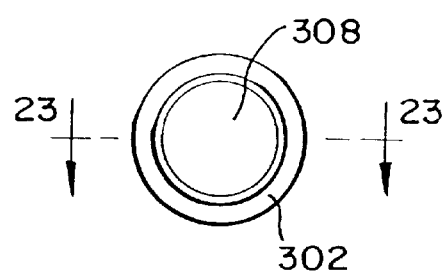
FIG. 22 is a top view of the key member.

Now referring to FIGS. 21–23, a key member 300 is shown as including a base portion 302 having a recess 304 shaped to receive the top of the container. The base portion is circular shaped and is open in the middle. The key member is mounted on the container by press fitting a circumferential flange 306, which forms the recess, about the container such that the valve stem and hub passes through an opening 308 formed in the middle of the key member. Alternatively, the key member can be mounted to the container with adhesive or other fasteners. The key member also includes a key portion 310 extending downwardly from the base portion. The key portion is preferably configured as a circular flange member, although other shapes would also work.

The indicator module shown in FIG. 21 has a recess 312 formed in an upper surface of the module housing. Preferably, the recess is formed as an arcuate shaped, or semi-circular, slot. The actuator member 314 extends upwardly from the module housing into the slot. The actuator member 314 is maintained substantially flush with or below the upper surface of the module 316. In this way, the actuator cannot be actuated by a user's finger or the like so as to inadvertently advance the indicator member and thereby provide an inaccurate reading of the number of dosages remaining in the container, or the number dispensed therefrom.

The shape or diameter of the key portion and recess are configured so that the key portion communicates with and is received in the recess formed in the module housing. When the container is mounted in the dispenser housing such that the valve stem is received in the well in the support block, the key portion is received in the recess and engages the actuator member.

In this way, key members having differently shaped key portions can be applied to containers holding different types of medicament so as to prevent the user from mixing up the containers and dispensers. In operation, a container having a certain key member with a specific key portion can be installed only in a dispenser housing having a recess shaped to receive that key portion. If the key portion does not fit the recess, the key ring will engage the upper surface of the module housing so as to prevent the actuation of the container relative to the dispenser housing and the attendant opening of the valve. This in turn prevents a user from installing containers having different medicaments in different dispensers, which could thereby adversely affect the counting of doses dispensed from the container, or the counting of the number of doses remaining therein. For example, a key member having a key portion with a thickness of 1 mm and an inner diameter of 13 mm is prevented from being installed in a recess having a width of 1 mm and an inner diameter of 15 mm, and vice versa.

Although the circular configuration of the key portion and slot shown in the figures is preferred since it allows the container to be rotated within the dispenser housing about its longitudinal axis, it should be understood that the key portion and slot, or like keyhole, can be shaped in any type of mating configuration and that the mating shapes are not limited to the circular configuration shown in the figures.

The indicator module provides an inexpensive and accurate device for counting dosages of medicament and the like. The module can be sized for easy installation as a separate unit in most conventional inhalation housings with minimal modification of the housing, including providing a viewing window in the housing in alignment with the module viewing window and the removal of any structure formed between the support block and outer wall of the housing. In addition, the module can be installed rearwardly of the support block so as not to interfere with or otherwise impede the air flow dispensing the medicament.

Although the present invention has been described with reference to preferred embodiments those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An aerosol dispenser for dispensing metered dosages of medicaments from a container having a valve stem extending longitudinally therefrom and moveable between a closed position and an open position, said container dispensing said metered dosage when said valve stem is moved to the open position, said aerosol dispenser comprising:

a housing adapted to support said container reciprocally moveable within said housing along a longitudinal axis, said housing having a well adapted to receive said valve stem and an exhaust port, said well communicating with said exhaust port such that said metered dosage of medicament is dispensed through said exhaust port when said valve stem is moved to the open position;

a ratchet wheel rotatably mounted in said housing and adapted to be responsive to the reciprocal movement of said container in said housing along said longitudinal axis such that said longitudinal movement of said container causes said ratchet wheel to rotate;

a worm rotatably mounted in said housing along a first rotation axis substantially perpendicular to the longitudinal axis of the movement of the container within the housing, said worm connected to said ratchet wheel such that rotation of said ratchet wheel causes said worm gear to rotate about said first rotation axis; and an indicator member comprising a circular gear engaging said worm, said circular gear mounted in said housing about a second axis of rotation substantially perpendicular to the longitudinal axis of the movement of the container within said housing and to the first rotation axis of the worm, said indicator member comprising dosage indicia visible to the user.

2. The dispenser of claim 1 further comprising an actuator member moveably mounted in said housing, said actuator member adapted to move in response to the movement of the container within said housing along said longitudinal axis and to operably engage said ratchet wheel so as to rotate said ratchet wheel in response to the longitudinal movement of the container within said housing.

3. The dispenser of claim 2 wherein said actuator member comprises an arm adapted to selectively engage and rotate said ratchet wheel.

4. The dispenser of claim 3 wherein said actuator member further comprises a ring adapted to engage the container, said ring moveably mounted in said housing, wherein said arm extends longitudinally from said ring.

5. The dispenser of claim 2 further comprising a spring biasing said actuator member away from said selective engagement with said ratchet wheel.

6. The dispenser of claim 5 wherein said actuator member comprises a post having an end adapted to operably engage said container and an arm adapted to selectively engage said ratchet wheel, said spring disposed about and engaging said post so as to bias said actuator member away from said selective engagement with said ratchet wheel.

7. The dispenser of claim 5 wherein said housing further comprises a viewing window, said dosage indicia visible to the user through said window.

8. The dispenser of claim 1 wherein said indicator member further comprises an indicator wheel coaxially mounted with said circular gear, said indicator wheel having said dosage indicia applied to a planar face of said indicator wheel so as to be visible to the user.

9. The dispenser of claim 1 wherein said ratchet wheel and said worm are coaxially mounted within said housing.

10. The dispenser of claim 1 further comprising a module mounted in said housing, wherein said ratchet wheel, said worm and said indicator member are rotatably mounted within said module.

11. The dispenser of claim 1 wherein said housing further comprises a mouthpiece, said mouthpiece forming said exhaust port.

12. An aerosol dispenser for dispensing metered dosages of medicaments from a container having a valve stem extending longitudinally therefrom and moveable between a closed position and an open position, said container dispensing said metered dosage when said valve stem is moved to the open position, said aerosol dispenser comprising:

a housing adapted to support said container reciprocally moveable within said housing along a longitudinal axis, said housing having a well adapted to receive said valve stem and an exhaust port, said well communicating with said exhaust port such that said metered dosage of medicament is dispensed through said exhaust port when said valve stem is moved to the open position;

a worm rotatably mounted in said housing about a first rotation axis transverse to said longitudinal axis, said worm adapted to be responsive to the reciprocal movement of said container in said housing along said longitudinal axis such that said longitudinal movement of said container causes said worm to rotate about said first rotation axis; and an indicator member comprising a circular gear engaging said worm, said circular gear mounted in said housing about a second axis of rotation transverse to the longitudinal axis of the movement of the container within said housing and to the first rotation axis of said worm, said indicator member comprising dosage indicia visible to the user.

13. The dispenser of claim 12 further comprising a ratchet wheel rotatably mounted in said housing coaxially with said worm, said ratchet wheel adapted to rotate in response to said longitudinal movement of said container with said housing.

14. The dispenser of claim 13 further comprising an actuator member moveably mounted in said housing, said actuator member adapted to move in response to the movement of the container within said housing along said longitudinal axis and to operably engage said ratchet wheel so as to rotate said ratchet wheel in response to the longitudinal movement of the container within said housing.

15. The dispenser of claim 14 wherein said actuator member further comprises a ring adapted to engage the container, said ring moveably mounted in said housing, wherein said arm extends longitudinally from said ring.

16. The dispenser of claim 14 further comprising a spring biasing said actuator member away from said selective engagement with said ratchet wheel.

17. The dispenser of claim 16 wherein said actuator member comprises a post having an end adapted to operably engage said container and an arm adapted to selectively engage the ratchet wheel, said spring disposed about and engaging said post so as to bias the actuator member away from said selective engagement with said ratchet wheel.

18. The dispenser of claim 12 wherein said indicator member further comprises an indicator wheel coaxially mounted with said circular gear, said indicator wheel having said dosage indicia applied to a face of said indicator wheel visible to the user.

19. The dispenser of claim 12 wherein said housing further comprises a viewing window, said dosage indicia visible to the user through said viewing window.

20. The dispenser of claim 12 wherein said housing further comprises a mouthpiece forming said exhaust port.

21. The dispenser of claim 12 further comprising a module mounted in said housing, wherein said worm and said indicator member are rotatably mounted within said module.

22. An inhalation device for dispensing metered dosages of medicaments from a container comprising:

a housing having a longitudinally extending cavity and a well located at a bottom of said cavity, said housing comprising a mouthpiece having an exhaust port communicating with said well;

said container comprising a valve stem extending longitudinally therefrom and moveable between a closed position and an open position, said container containing a plurality of metered dosages of medicaments, said valve stem dispensing one of said plurality of said metered dosages when said valve stem is moved to the open position, said container disposed in said cavity of said housing such that said valve stem is received within said well, said container reciprocally moveable within said housing along said longitudinal extent of the cavity such that said valve stem is moved between said open and closed position by engagement with said well;

a ratchet wheel rotatably mounted in said housing;

an actuator member moveably mounted within said housing and comprising an arm having an end portion selectively engaging said ratchet wheel in response to the reciprocal movement of said container in said housing along said longitudinal axis such that said longitudinal movement of said container and said actuator arm causes said ratchet wheel to rotate about a first rotation axis;

a worm rotatably mounted in said housing along said first rotation axis transverse to the longitudinal axis of the movement of the container within the housing, said worm coaxially mounted to said ratchet wheel such that rotation of said ratchet wheel in response to the selective engagement of said arm of said actuator member causes said worm gear to rotate about said first rotation axis; and an indicator member comprising a circular gear engaging said worm and a indicator wheel coaxially mounted to said circular gear, said circular gear and said indicator wheel mounted to said housing on an axle defining a second axis of rotation transverse to the longitudinal axis of the movement of the container within the housing and to the first rotation axis of the worm, said indicator wheel having a planar face comprising dosage indicia visible to the user.

23. An indicator module adapted to be received within a aerosol dispenser housing for indicating the number of metered dosages of medicaments dispensed from a container disposed within said dispenser housing and having a valve stem extending longitudinally therefrom and moveable between a closed position and an open position along a longitudinal axis, said container dispensing said metered dosage when said valve stem is moved to the open position, said dispenser housing comprising a wall and a support block supporting said valve stem spaced apart from said wall, said indicator module comprising:

a key member adapted to be mounted to said container;

a module housing adapted to be received within said dispenser housing between said support block and said wall of said housing, wherein said module housing has a passageway shaped to receive at least a portion of said key member as said container is disposed in said dispenser housing; and an indicator member mounted in said module housing, said indicator member comprising dosage indicia.

24. The indicator module of claim 23 wherein said module further comprises an actuator member adapted to engage said container, said actuator member moveable within said module housing and adapted to selectively move said indicator member in response to the longitudinal movement of said container relative to said dispenser housing.

25. The indicator module of claim 24 wherein said module further comprises a worm rotatably mounted in said module housing about a first axis, said worm engaging said indicator member, said actuator member adapted to selectively rotate said worm in response to the longitudinal movement of the container within the housing.

26. The indicator module of claim 25 further comprising a spring disposed within said module housing and engaging said actuator member so as to bias said actuator member upwardly within said module housing and into engagement with said container.

27. The indicator module of claim 26 wherein said actuator member further comprises a stop surface and wherein said spring engages said stop surface so as to bias said actuator member upwardly within said enclosure.

28. The indicator module of claim 24 wherein said indicator member further comprises a gear engaging said worm, said gear mounted in said module housing about a second axis of rotation transverse to the first axis of the worm.

29. The indicator module of claim 23 wherein said module housing comprises a first and second member joined to form an enclosure.

30. The module of claim 23 further comprising a viewing window formed in said module housing.

31. An aerosol dispenser for dispensing metered dosages of medicaments from a container having a valve stem extending longitudinally therefrom and moveable between a closed position and an open position, said container dispensing said metered dosage when said valve stem is moved to the open position, said aerosol dispenser comprising:

a housing adapted to support said container reciprocally moveable within said housing along a longitudinal axis, said housing having a well adapted to receive said valve stem and an exhaust port, said well communicating with said exhaust port such that said metered dosage of medicament is dispensed through said exhaust port when said valve stem is moved to the open position;

a worm rotatably mounted in said housing about a first rotation axis transverse to said longitudinal axis, said worm adapted to be responsive to the reciprocal movement of said container in said housing along said longitudinal axis such that said longitudinal movement of said container causes said worm to rotate about said first rotation axis; and an indicator member comprising a circular gear engaging said worm, said circular gear mounted in said housing on an axle forming a second axis of rotation transverse to the first rotation axis of the worm and non-parallel to the longitudinal axis of the movement of the container within the housing, said indicator member comprising dosage indicia visible to the user.

32. A method for dispensing metered dosages of medicaments from a container having a valve stem extending longitudinally therefrom and moveable between a closed position and an open position, said container dispensing said metered dosage when said valve stem is moved to the open position, said method comprising the steps of:

providing a housing having a well and an exhaust port, said well communicating with said exhaust port;

providing said container filled with a predetermined number of said metered dosages, said container moveably supported in said housing along a longitudinal axis, said container comprising a valve stem received within said well of said housing and moveable between a closed and open position as said container is moved longitudinally within said housing, said container adapted to discharge one of said metered dosages when said valve stem is moved to the open position;

moving said container along said longitudinal axis so as to move said valve stem to the open position and thereby discharge one of said metered dosages through said well and said port;

rotating a worm mounted in said housing a predetermined angular amount in response to said longitudinal movement of said container, said worm mounted along an axis transverse to said longitudinal axis of said movement of said container within said housing;

providing an indicator member mounted in said housing about an axis transverse to the longitudinal axis and to said axis of said worm, said indicator member comprising a circular gear;

engaging said circular gear with said worm so as to rotate said circular gear about said axis transverse to said longitudinal axis and to said axis of said worm; and providing indicia on said indicator member to indicate the number of metered dosages remaining in or dispensed from said container.

33. The method of claim 32 further comprising the steps of providing a ratchet wheel coaxially mounted to said worm in said housing and rotating said ratchet wheel so as to rotate said worm.

34. The method of claim 33 further comprising the steps of engaging an actuator member with said container such that actuator member moves in response to the movement of the container within the housing along said longitudinal axis, and engaging said ratchet wheel with said actuator member so as to rotate said ratchet wheel in response to the longitudinal movement of the container within the housing.

35. The method of claim 34 wherein said actuator member comprises an arm having an end adapted to selectively engage and rotate the ratchet wheel.

36. The method of claim 35 wherein said actuator member further comprises a ring adapted to engage the container, said ring moveably mounted in said housing and wherein said arm extends longitudinally from said ring.

37. The method of claim 35 further comprising a spring biasing actuator away from said selective engagement with said ratchet wheel.

38. The method of claim 37 further comprising a post member mounted within said housing, said spring disposed on said post member.

39. The method of claim 33 wherein said indicator member further comprises a indicator wheel coaxially mounted with said circular gear, said indicator wheel having said indicia applied to a face of the indicator wheel visible to the user.

40. The method of claim 33 wherein said housing further comprises a viewing window, said indicia visible to the user through said window.

41. The method of claim 33 wherein said ratchet wheel and said worm are coaxially mounted within said housing.

42. An apparatus for dispensing metered dosages of medicaments from a container, said apparatus comprising:
 a dispenser housing comprising a support block and a wall spaced apart from said support block, said support block having a well and an orifice communicating with said well, said dispenser housing having a cavity formed above said support block;
 said container comprising a valve stem, wherein said container is disposed in said cavity and said valve stem is mounted in said well of said support block;
 a dose indicator module for indicating the number of metered doses remaining in or dispensed from said container, said dose indicator module comprising a module housing mounted in said dispenser housing below said container in the space between said support block and said dispenser housing wall, wherein said module housing has a passageway formed therein; and
 a key member mounted to said container, said key member shaped to be received in said passageway as said valve stem of said container is mounted in said support block.

43. The apparatus of claim 42 wherein said dose indicator module further comprises an indicator member visible to a user for indicating the number of metered doses remaining in or dispensed from said container.

44. The apparatus of claim 43 wherein said dispenser housing further comprises a viewing window, wherein said indicator member is visible to the user through the viewing window.

45. The apparatus of claim 43 wherein said dose indicator module further comprises a worm rotatably mounted in said module housing about a first axis, said worm engaging said indicator member.

46. The apparatus of claim 45 further comprising a ratchet wheel coaxially mounted in said module with said worm.

47. The apparatus of claim 46 further comprising an actuator member comprising a post member protruding from said module housing, said post member adapted to engage said container, said actuator member moveable within said module housing and selectively engaging said ratchet wheel.

48. The apparatus of claim 47 further comprising a spring disposed within said module housing and engaging said actuator member so as to bias said post member upwardly within said module housing.

49. The apparatus of claim 42 wherein said module housing comprises a first and second member joined to form an enclosure.

50. The apparatus of claim 42 wherein said indicator module further comprises an actuator member extending into said passageway, wherein said key member engages said actuator member when said key member is received in said passageway.

51. The apparatus of claim 50 wherein said indicator module housing comprises an upper surface and wherein said actuator member does not extend beyond said upper surface when disengaged from said key member.

52. The apparatus of claim 42 wherein said passageway comprises a slot.

53. The apparatus of claim 52 wherein said slot is arcuate shaped and wherein said key member comprises a base portion mounted to said container and a key portion extending from said base portion, said key portion shaped to be received within said groove.

54. The apparatus of claim 53 wherein said key portion comprises a circular flange.

* * * * *

UNITED STATES PATENT AND TRADEMARK OFFICE
CERTIFICATE OF CORRECTION

PATENT NO. : 6,142,339
DATED : November 7, 2000
INVENTOR(S) : Richard Blacker et al.

It is certified that error appears in the above-identified patent and that said Letters Patent is hereby corrected as shown below:

Title page,
Item [73], change "London, Canada" to -- London, Ontairo, Canada --.

Claim 22,
Line 38, change "a" to -- an --.

Claim 23,
Line 1, change "a" to -- an --.

Claim 39,
Line 2, change "a" to -- an --.

Signed and Sealed this

Fourth Day of December, 2001

Attest:

*Nicholas P. Godici*

NICHOLAS P. GODICI
*Attesting Officer*   *Acting Director of the United States Patent and Trademark Office*